United States Patent
Guerreiro et al.

(10) Patent No.: US 12,428,677 B2
(45) Date of Patent: Sep. 30, 2025

(54) THERMALLY RESPONSIVE CONJUGATES FOR DNA POLYMERASE INHIBITION

(71) Applicant: Tozaro Limited, Sharnbrook (GB)

(72) Inventors: Antonio Guerreiro, Cranfield (GB); Francesco Canfarotta, Oadby (GB); Adrian Kinkaid, Saffron Walden (GB); Alistair Groves, Rushden (GB)

(73) Assignee: Tozaro Limited, Sharnbrook (GB)

( * ) Notice: Subject to any disclaimer, the term of this patent is extended or adjusted under 35 U.S.C. 154(b) by 829 days.

(21) Appl. No.: 17/755,083

(22) PCT Filed: Oct. 21, 2020

(86) PCT No.: PCT/EP2020/079657
§ 371 (c)(1),
(2) Date: Apr. 20, 2022

(87) PCT Pub. No.: WO2021/078813
PCT Pub. Date: Apr. 29, 2021

(65) Prior Publication Data
US 2022/0372549 A1    Nov. 24, 2022

(30) Foreign Application Priority Data
Oct. 21, 2019  (EP) ..................................... 19204366

(51) Int. Cl.
C12P 19/34    (2006.01)
C12Q 1/686    (2018.01)
C12Q 1/6848   (2018.01)

(52) U.S. Cl.
CPC ........... *C12Q 1/686* (2013.01); *C12Q 1/6848* (2013.01)

(58) Field of Classification Search
CPC .................................................. C12Q 1/6844
See application file for complete search history.

(56) References Cited

U.S. PATENT DOCUMENTS

| | | | |
|---|---|---|---|
| 5,338,671 A | 8/1994 | Scalice et al. | |
| 5,693,502 A | 12/1997 | Gold et al. | |
| 5,998,588 A * | 12/1999 | Hoffman ............ | A61K 47/6891 424/193.1 |

FOREIGN PATENT DOCUMENTS

| | | |
|---|---|---|
| CN | 101239189 A | 8/2008 |
| EP | 2246701 A1 | 3/2010 |
| WO | 1997009068 A2 | 3/1997 |
| WO | 2001051092 A2 | 7/2001 |
| WO | 2004014969 A1 | 2/2004 |
| WO | 2006074217 A2 | 7/2006 |
| WO | 2007038422 A2 | 4/2007 |
| WO | 2010101627 A2 | 9/2010 |

OTHER PUBLICATIONS

Cui et al., ACS Applied Materials and Interfaces 7, 21913-21918 (2015) (Year: 2015).*
Anonymous, Reverse-Transcriptase Inhibitor, pp. 9, Wikipedia, Jul. 6, 2021.
Anonymous, Temperature-Responsive Polymer, pp. 12, Wikipedia, Jun. 19, 2021.
Bourke, et al., NaOH Treatment to Neutralize Inhibitors of Taq Polymerase, J. Forensic Sci. 44(5): 1046-1050 (1999).
Karolewicz, A Review of Polymers as Multifunctional Excipients in Drug Dosage Form Technology, Saudi Pharn J. 24: 525-536 (2016).
Mallipeddi, et al., Progress in Antiretroviral Drug Delivery using Nanotechnology, Int. J. Nanomedicine 5: 533-547 (2010).
Pungitore, et al., Inhibition of Taq DNA Polymerase by Catalpol, Cell. Mol. Biol. 50(6): 767-772 (2004).
WIPO, PCT Form ISA210, International Search Report for IA Serial No. PCT/EP2020/079657, pp. 6 (mailed Dec. 23, 2020).
WIPO, PCT Form ISA237 Written Opinion for IA Serial No. PCT/EP2020/079657, pp. 8 (mailed Dec. 23, 2020).
WIPO, PCT Form IPEA416 International Preliminary Report on Patentability for IA Serial No. PCT/EP2020/079657, pp. 29 (mailed Feb. 4, 2022).
Zhang, et al., Thermoresponsive Polymers with Lower Critical Solution Temperature: From Fundamental Aspects and Measuring Techniques to Recommended Turbidimetry Conditions, Mater. Horiz. 4: 109-116 (2017).
EPO, Examination Report for European patent 20790358.4 (mailed Feb. 3, 2025).
JPO, Examination Report for Japanese patent 2022-523464 (mailed Oct. 29, 2024).

* cited by examiner

*Primary Examiner* — Kenneth R Horlick
(74) *Attorney, Agent, or Firm* — UltimatEdge IP Law Group. P.C.; Dean G. Stathakis

(57) ABSTRACT

A method of amplifying a target nucleic acid in a DNA sample comprising (a) contacting the DNA sample containing the target nucleic acid with a DNA polymerase, at least two oligonucleotide primers designed to flank the target nucleic acid, a mixture of dATP, dGTP, dCTP, and dTTP, and a conjugate comprising a DNA polymerase inhibitor covalently attached to a negative temperature sensitive polymer, (b) heating the output of step (a) to a temperature at which the conjugate precipitates and thus the DNA polymerase is no longer inhibited and (c) amplifying the target nucleic acid, e.g. by performing PCR steps of denaturing the target nucleic acid, annealing the primers to the target nucleic acid, and extending the primers, wherein step (c) is repeated at least two times. Also provided is a conjugate comprising a DNA polymerase inhibitor covalently attached to a negative temperature sensitive polymer and kits and aqueous compositions comprising the same.

20 Claims, 2 Drawing Sheets

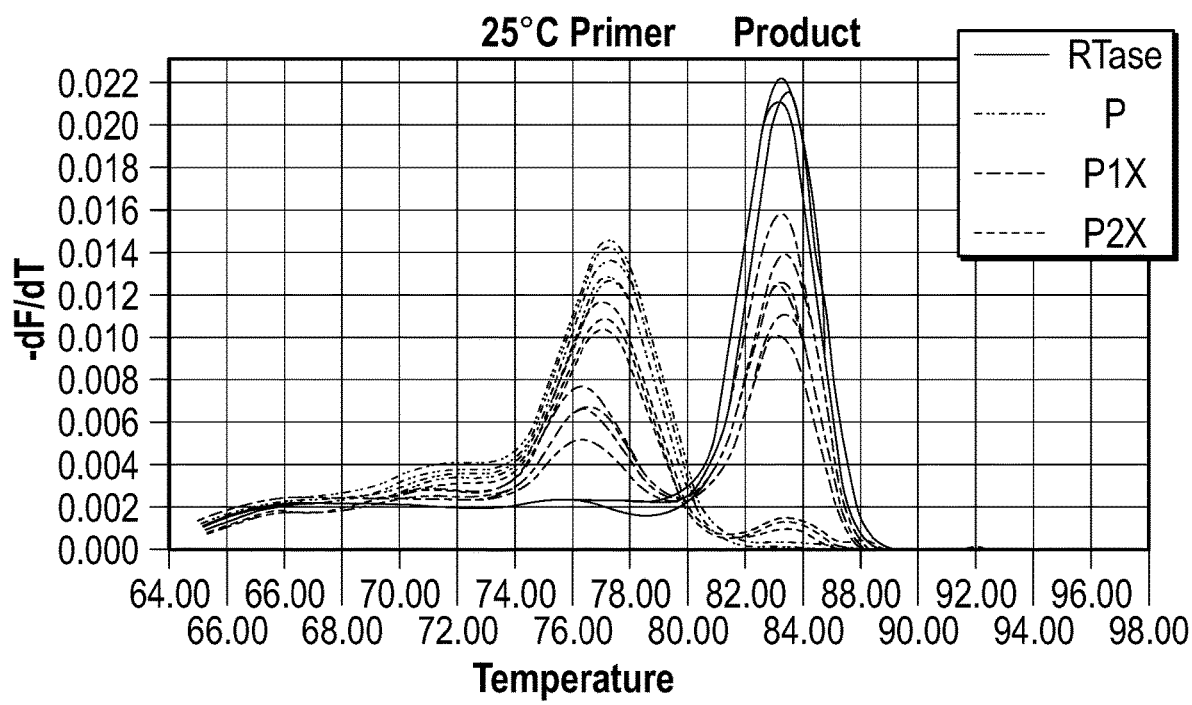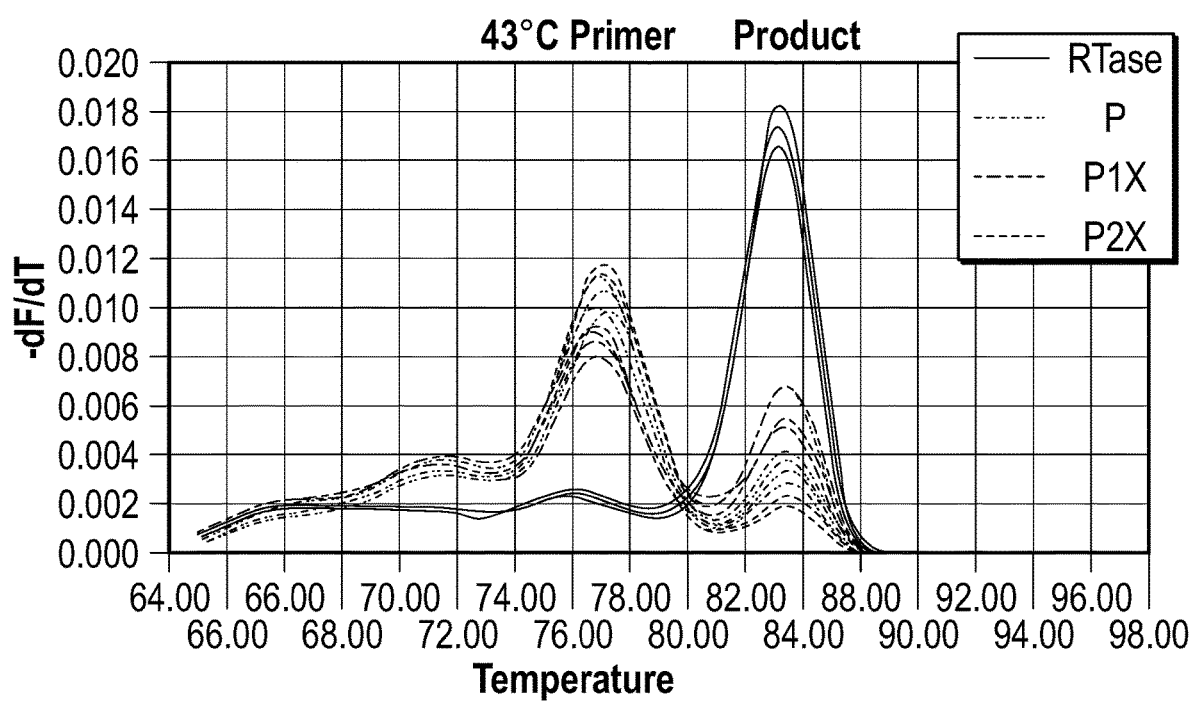

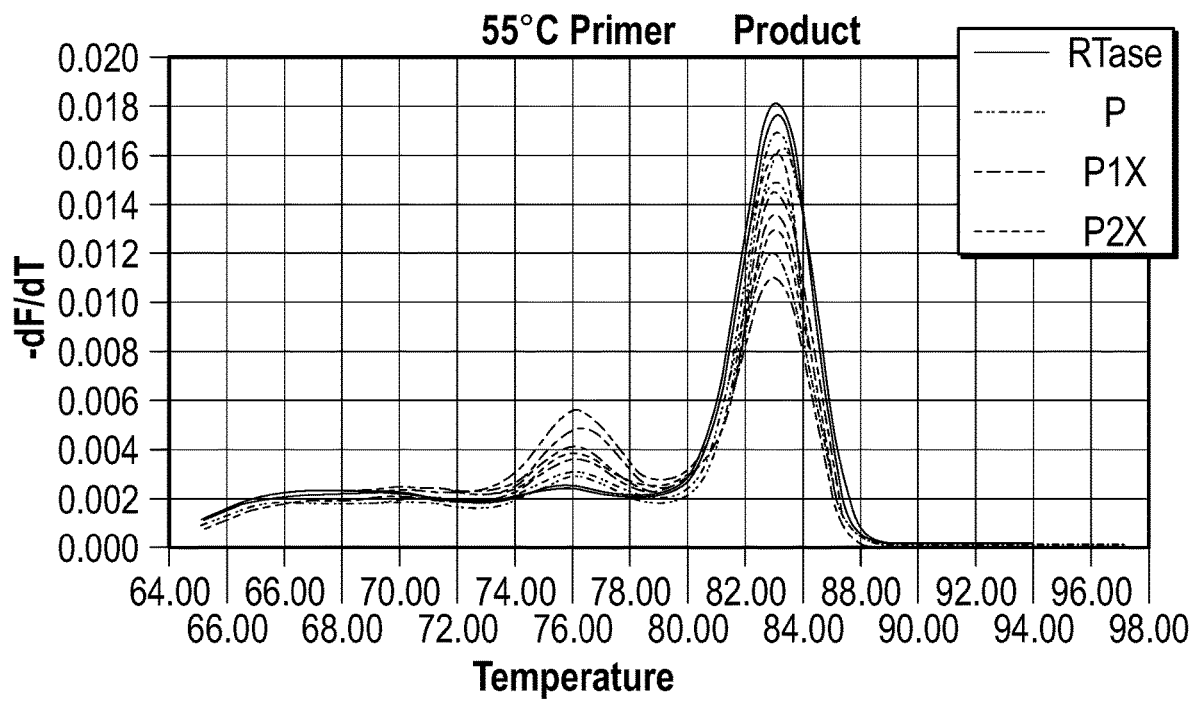
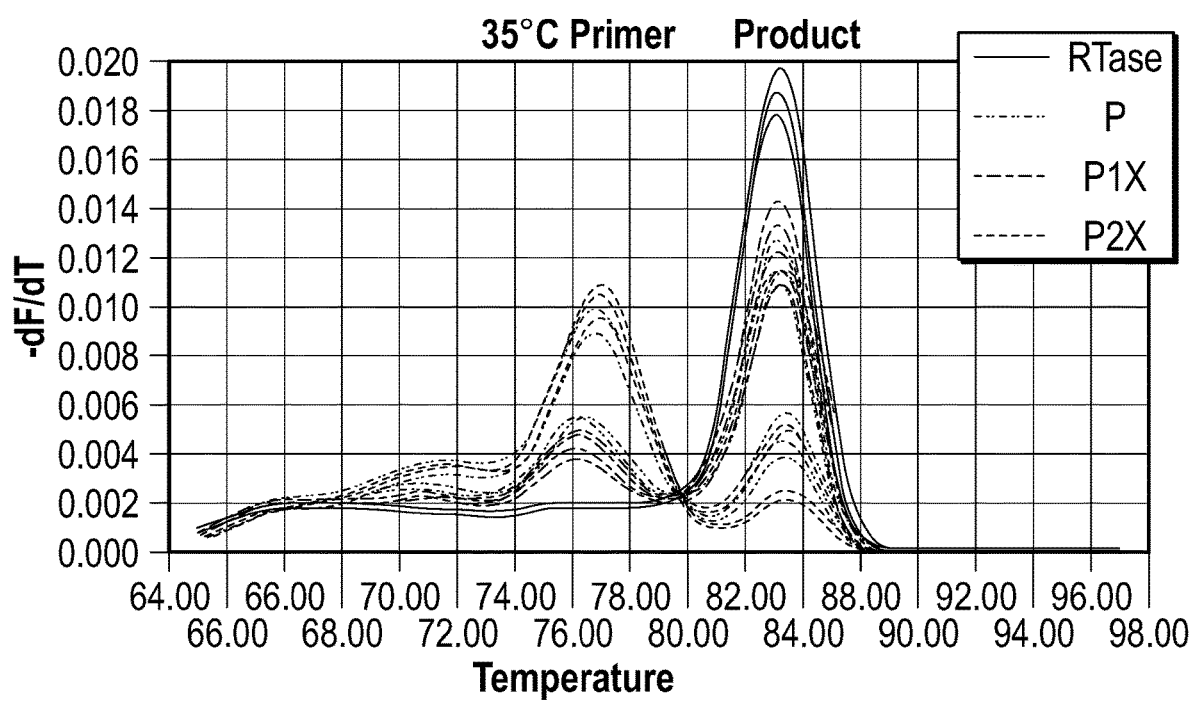
(Continued)

THERMALLY RESPONSIVE CONJUGATES FOR DNA POLYMERASE INHIBITION

The present invention relates to a conjugate for use in nucleic acid amplification, a composition comprising a DNA polymerase bound to said conjugate, a kit comprising a DNA polymerase and said conjugate and to a method of amplifying a target nucleic acid in a DNA sample using said conjugate.

BACKGROUND TO THE INVENTION

Smart polymers, also known as phase transition polymers or stimuli responsive polymers, are polymers which respond to their environment by changing their physical and/or chemical properties. Smart polymers can be responsive to a number of different environmental factors including temperature, humidity, pH, chemical compounds, the wavelength or intensity of light or an electrical or magnetic field and can respond in various ways for example by changing their shape, colour or their solubility status. At critical points, slight changes in the environment are sufficient to induce significant changes in the physical and/or chemical properties of the smart polymer thus smart polymers can exhibit a discontinuous response to slight changes in their environment.

In recent years, smart polymers have gained significant interest due to their use in a variety of applications such as in smart biocatalysts, where they are conjugated to enzymes, or in biomedicine for specifically targeted drug delivery.

Another application of smart polymers has been in the field of polymerase chain reaction (PCR). In September 2015, Chen at al reported in ACS publications (paper entitled: Improvement in the Thermal Stability of Pyrophosphatase by Conjugation to Poly(N-isopropylacrylamide): Application to the Polymerase Chain Reaction) that the thermally responsive polymer poly(N-isopropylacrylamide) (PNIPAM) had been conjugated to pyrophosphatase (PPase) in an attempt to improve the heat resistance of the enzyme and thus preserve its activity at elevated temperatures, such as those used in the extension phase of a PCR reaction. The optimum temperature of the PPase-PNIPAM conjugate, when compared to the unconjugated free enzyme, was shown to increase from 45 to 60° C. Furthermore, after incubation at 60° C. for 3 hours, 77% enzyme activity was retained for the PPase-PNIPAM conjugate, representing a 6.8-fold increase as compared to the unconjugated free enzyme. When used in PCR, the PPase-PNIPAM conjugate produced yields 1.5-fold higher than when only unconjugated free enzyme was used.

Heat sensitivity of PPase is however not the only problem with PCR. A further problem arises from the ability of DNA polymerase enzymes to catalyse (1) the extension of partially annealed primers to non-specific sites in DNA at room temperature e.g. when the PCR reaction components are being combined and the reaction is being set up and (2) the extension of primer dimers. Although the efficiency of thermostable DNA polymerases commonly used in PCR reactions is lower at room temperature than it is at higher temperatures e.g. those used in the extension phase of a PCR reaction, there is still a small amount of activity at room temperature. When the intended target nucleic acid is present in high concentrations, non-specific amplification is not a major issue; however, when the target nucleic acid is present in much lower concentrations, non-specific amplification can be a much bigger issue because it can severely compromise the detection of the desired target nucleic acid.

Several methods have been developed in order to reduce non-specific amplification. The collective name for such methods is Hot Start PCR. The principle behind Hot Start PCR is to keep the DNA polymerase in an inactive state until the temperature of the reaction is above primer annealing temperature, and this has been achieved in numerous ways.

The first method is primitive and advocates keeping all PCR reaction vessels on ice and then transferring them to a thermocycler already set to 95° C. A slight modification of the aforementioned method sees the DNA polymerase omitted from the reaction set up and only added after the PCR reaction vessels are in the thermocycler set to 95° C. However, this is difficult to execute and runs the risk of contamination/loss of reaction components when the PCR reaction vessels are opened.

More advanced methods include physically isolating the DNA polymerase from the other PCR reaction components e.g. by freezing the PCR reaction components excluding the DNA polymerase and then adding the DNA polymerase in liquid state. As the frozen layer melts, the DNA polymerase mixes with the other PCR reaction components. Other means of separating the DNA polymerase from the other PCR reaction components include using wax beads or petroleum jelly.

The most recent methods involve inhibition of the DNA polymerase enzyme. Two types of inhibitors are known to date, antibodies and oligonucleotides.

U.S. Pat. No. 5,338,671 describes a method for the amplification of a target nucleic acid comprising the step of contacting a specimen suspected of containing a target nucleic acid with PCR reagents including a temperature sensitive inhibitor of DNA polymerase, wherein said inhibitor is an antibody which is specific to the DNA polymerase and which inhibits the DNA polymerase at a temperature T1 which is less than about 85° C. and which is irreversibly inactivated at temperature T2 which is greater than T1 and also greater than about 40° C. Thus, the antibody works by inhibiting the DNA polymerase until the temperature of the PCR is such that the antibody is irreversibly denatured. At that point the DNA polymerase becomes uninhibited. However, whilst the method is useful, disadvantages with this approach remain. The first is the high cost associated with antibody use, the second is the requirement for an antibody for each different enzyme and the third is that the antibody-DNA polymerase is only slowly disrupted by an increase in temperature and thus it is not possible to control the specific temperature at which the polymerase becomes activated. A further disadvantage is that the antibody is irreversibly denatured and thus the DNA polymerase is only inhibited at the beginning of the PCR reaction not during the PCR reaction.

U.S. Pat. No. 5,693,502 describes a method for performing PCR comprising the steps of (1) mixing a sample containing a target nucleic acid with a single-stranded nucleic acid ligand which is capable of inhibiting the DNA polymerase in a temperature dependent manner, (2) heating the mixture to a temperature at which the nucleic acid no longer inhibits the DNA polymerase and (3) performing PCR. Whilst nucleic acid ligands are cheaper than antibodies, disadvantages still remain, namely that the nucleic acid-DNA polymerase is only slowly disrupted by an increase in temperature and thus it is not possible to control the specific temperature at which the polymerase becomes activated. Also, inhibition is only effective at or slightly above room temperature. Hence, this technology does not provide a complete hot-start.

Accordingly, one aim of the present invention is to provide alternative methods and reagents for amplifying target nucleic acids. A further aim is to provide improved methods and reagents for amplifying target nucleic acids. A related aim is to provide conjugates for use in such methods and aqueous solutions and kits comprising said conjugates.

SUMMARY OF INVENTION

Accordingly, the invention provides a method of amplifying a target nucleic acid in a DNA sample comprising:
(a) contacting the DNA sample containing the target nucleic acid with:
  (i) a DNA polymerase,
  (ii) at least two oligonucleotide primers designed to flank the target nucleic acid,
  (iii) a mixture of dATP, dGTP, dCTP, and dTTP, and
  (iv) a conjugate comprising a DNA polymerase inhibitor covalently attached to a negative temperature sensitive polymer,
(b) heating the output of step (a) to a temperature at which the conjugate precipitates and thus the DNA polymerase is no longer inhibited,
(c) amplifying the target nucleic acid, e.g. by performing PCR steps of denaturing the target nucleic acid, annealing the primers to the target nucleic acid, and extending the primers,
wherein step (c) is repeated at least two times.

Also provided is a conjugate comprising a DNA polymerase inhibitor covalently attached to a negative temperature sensitive polymer.

Further provided is a kit comprising
(a) a DNA polymerase, and
(b) a conjugate comprising a DNA polymerase inhibitor covalently attached to a negative temperature sensitive polymer.

Still further provided is an aqueous composition comprising (i) a DNA polymerase bound to (ii) a conjugate comprising a DNA polymerase inhibitor covalently attached to a negative temperature sensitive polymer.

In use of the invention, for example prior to DNA amplification by PCR and with reagents present and at room temperature (20° C.), the conjugates is in solution and the inhibitor portion is bound to and inhibiting the activity of the DNA polymerase. Raising the temperature proceeds with the conjugate remaining in solution until it precipitates, taking the inhibitor out of solution and releasing the DNA polymerase.

Suitably, the conjugate precipitates at a temperature between 35° C. and 65° C., preferably between 40° C. and 60° C., more preferably between 45° C. and 55° C.

DETAILS OF THE INVENTION

The invention provides a method of amplifying a target nucleic acid in a DNA sample comprising:
(a) contacting the DNA sample containing the target nucleic acid with:
  (i) a DNA polymerase,
  (ii) at least two oligonucleotide primers designed to flank the target nucleic acid,
  (iii) a mixture of dATP, dGTP, dCTP, and dTTP, and
  (iv) a conjugate comprising a DNA polymerase inhibitor covalently attached to a negative temperature sensitive polymer,
(b) heating the output of step (a) to a temperature at which the conjugate precipitates and thus the DNA polymerase is no longer inhibited,
(c) amplifying the target nucleic acid, e.g. by performing PCR steps of denaturing the target nucleic acid, annealing the primers to the target nucleic acid, and extending the primers, wherein step (c) is repeated at least two times.

Typically, the amplification is carried out in aqueous buffer. Hence, the method may comprise amplifying a target nucleic acid in a DNA sample comprising
(a) contacting the DNA sample containing the target nucleic acid with a composition comprising:
  (i) a DNA polymerase,
  (ii) at least two oligonucleotide primers designed to flank the target nucleic acid,
  (iii) a mixture of dATP, dGTP, dCTP, and dTTP,
  (iv) an aqueous buffer, and
  (v) a conjugate comprising a DNA polymerase inhibitor covalently attached to a negative temperature sensitive polymer,
(b) heating the output of step (a) to a temperature at which the conjugate precipitates and thus the DNA polymerase is no longer inhibited, and
(c) performing standard PCR steps of denaturing the target nucleic acid, annealing the primers to the target nucleic acid, and extending the primers,
wherein step (c) is repeated at least two times.

In an example carried out to illustrate the invention, described below in more detail, a DNA polymerase was reversibly inhibited using a conjugate of the invention in an RTase reaction, prior to DNA amplification of cDNA. As will be appreciated, a use of the invention lies in improved DNA amplification reactions. Presence of the inhibitor, at room temperature and at higher temperatures though below the typical primer annealing temperature used in PCR reactions, reduces formation of unwanted products that might contaminate the PCR reaction output. For example, non-specific binding of primers at lower temperatures can result in amplification of sequences other than the target when DNA polymerase is present and active. The conjugate of the invention prevents this.

The method of the invention uses a conjugate comprising a DNA polymerase inhibitor covalently attached to a negative temperature sensitive polymer. Hence, the invention also provides a conjugate comprising a DNA polymerase inhibitor covalently attached to a negative temperature sensitive polymer.

The DNA polymerase inhibitor may inhibit DNA or RNA directed DNA polymerases which catalyse the synthesis of a DNA molecule either from a DNA template or an RNA template respectively.

Examples of DNA polymerases which are suitable as targets for inhibitors used in the conjugate of the invention which is in turn used in the method of the invention include those isolated from *Thermus aquaticus, Pyrococcus furiosus, Thermococcus kodakaraensis Thermus thermophilus, Pyrococcus woesei, Thermus filiformis, Thermus flavus, Thermus ubiquitous, Thermus litoralis, Thermotoga maritima*, or recombinant versions of any of the aforementioned DNA polymerases.

Examples of inhibitors of DNA polymerase include vidarabine, lamivudine, rifamycin SV monosodium salt, neobavaisoflavone, hexaprenylhydroquinone, abacavir hemisulfate, aphidicolin, mithramycin A, tenofovir and thiolutin.

In a preferred embodiment of the invention, the inhibitor is Zidovudine.

Although examples of DNA polymerase inhibitors have been specified, the type of inhibitor used to inhibit the DNA polymerase, and indeed its mechanism of action, is not critical. The inhibitor may inhibit the DNA polymerase in a competitive or non-competitive manner. PCR is a technique well known to those skilled in the art. In order to test whether a given candidate inhibitor inhibits DNA polymerase, a PCR reaction can be carried out with a candidate inhibitor and also with a known inhibitor (positive control) and with no inhibitor (negative control), using a known target DNA, primers for the target and standard reagents and under standard conditions, for at least 25 cycles. Presence of a product (for the negative control reaction) confirms that the DNA polymerase is active and thus absence of a product for the candidate inhibitor indicates the candidate is indeed an inhibitor of DNA polymerase. Absence of product in this context refers to formation of product at 25% or less, preferably 10% or less than for the negative control.

The conjugate of the invention which is used in the method of the invention comprises a negative temperature sensitive polymer, a specific type of thermally responsive polymer.

Thermally responsive polymers, also known as temperature-responsive polymers, are polymers that exhibit a drastic and discontinuous change in their physical or chemical properties in response to temperature change.

In the conjugate of the invention which is used in the method of the invention it is the solubility of the thermally responsive polymer, and thereby the conjugate, that is sensitive to temperature.

Thermally responsive polymers that change their solubility status in response to changes in temperature can be categorised into two classes: the first class comprising thermally responsive polymers that become insoluble above a critical temperature called the lower critical solution temperature (LCST), and the second class comprising thermally responsive polymers that precipitate and undergo phase change below a critical temperature known as the upper critical solution temperature (UCST).

When polymers exhibiting LCST are dissolved in an aqueous system, they are generally completely miscible below the LCST, but their solubility in aqueous solution decreases with increases in temperature; above a critical value, i.e. the LCST, they show phase separation and the polymer chains show coil-to-globule-to-aggregate transition. Polymers exhibiting LCST are also known as "negative temperature sensitive polymers". Examples of LCST polymers include poly(N-isopropylacrylamide) (PNIPAAm), polyvinylcaprolactam (PNVCL), poly(N,N-diethyl acrylamide) (PDEAM), poly(N-ethylmethacrylamide) (PNEMAM), poly (methyl vinyl ether) (PMVE) and poly(2-ethoxyethyl vinyl ether) (PEOVE).

Thermally responsive polymers which show UCST are referred to as "positive temperature sensitive polymers". These polymers, above a certain temperature, remain miscible in solution but as the temperature of the solution falls below a critical value, i.e. the UCST, phase separation occurs. Examples of UCST polymers include poly(acrylic acid) (PAA), polyacrylamide (PAAm), and poly(acrylamide-co-butyl methacrylate).

The LCST or UCST is an intrinsic property of the thermally responsive polymer, which is unchanged if the polymer is simply mixed with an inhibitor e.g. a DNA polymerase inhibitor. However, the LCST or UCST can be changed if the polymer is chemically conjugated to an inhibitor e.g. a DNA polymerase inhibitor. Changes in the LCST or UCST depend on the nature of the inhibitor e.g. the DNA polymerase inhibitor.

With respect to LCST polymers, if the inhibitor is hydrophilic, the LCST typically goes up and thus a higher temperature is needed to precipitate the conjugate from the solution phase. Conversely, if the inhibitor is hydrophobic, the LCST typically goes down.

With respect to UCST polymers, if the inhibitor is hydrophilic, the UCST typically goes down and thus a lower temperature is needed for the conjugate to go into solution. Conversely, if the inhibitor is hydrophobic, the UCST typically goes up.

As noted above, a key feature of thermally responsive polymers is that they exhibit a drastic and discontinuous change in their physical or chemical properties in response to temperature change.

When thermally responsive polymers are covalently conjugated to an inhibitor such as an inhibitor of DNA polymerase, this feature can be substantially conferred upon the entirety of the conjugate i.e. the conjugate also exhibits a drastic and discontinuous change in its physical or chemical properties in response to temperature change.

In the present invention, it is advantageous to be able to tightly control when a DNA polymerase enzyme is active and when it is inhibited.

Herein, reference to the LCST is reference to the LCST of the conjugate, not the isolated (non-conjugated polymer). Accordingly, in the conjugate of the invention used in the method of the invention and in which the thermally responsive polymer is a negative temperature sensitive polymer, 5° C. above the LCST (i.e. precipitation temperature), 10% or less of the conjugate is in solution and 5° C. below the LCST (i.e. precipitation temperature), 90% or more of the conjugate is in solution. More preferably, 2° C. above the LCST (i.e. precipitation temperature), 10% or less of the conjugate is in solution and 2° C. below the LCST (i.e. precipitation temperature), 90% or more of the conjugate is in solution. Even more preferably, 1° C. above the LCST (i.e. precipitation temperature), 10% or less of the conjugate is in solution and 1° C. below the LCST (i.e. precipitation temperature), 90% or more of the conjugate is in solution.

In a preferred embodiment of the invention the negative temperature sensitive polymer is, or comprises, a polymer selected from: Poly(N-substituted acrylamide)s and its derivatives, Poly(methyl vinyl ether), Poly(N-vinylcaprolactam), Poly(2-substituted 2-oxazoline)s and its derivatives, Poly(2-substituted 2-oxazine)s and its derivatives, hydroxypropyl cellulose, hydroxypropylmethyl cellulose, ethylhydroxyethyl cellulose, hydroxyethyl cellulose, poly (asparagine) peptides and its derivatives. Most preferably, the negative temperature sensitive polymer is poly(N-isopropylmethacrylamide) also referred to as PNiPMAM.

The size i.e. molecular weight of the negative temperature sensitive polymer may be in the range up to 200 KDa; the range may be 200 KDa to 10 KDa. That said, suitably the negative temperature sensitive polymer will have a molecular weight of less than 200 KDa, more suitably less than 100 KDa, and may be less than 50 KDa, or less than 20 KDa. In some preferred embodiments, the negative temperature sensitive polymer component of the conjugate of the invention used in the method of the invention is chosen so as to be relatively small/short so as to minimise the amount of material used, without compromising the sensitivity of the polymer. For some polymers, e.g. acrylamide derivatives, the LCST does not change significantly with molecular weight or polymer concentration so a range of sizes/weights can be used.

Suitable methods for determining the size of thermally responsive polymers e.g. negative temperature sensitive polymers used in the conjugate of the invention which is in turn used in the method of the invention include polymer membrane osmometry, gel permeation chromatography, viscosity analysis, mass spectrometry, end-group analysis by e.g. NMR and static light scattering.

One consideration that needs to be borne in mind when selecting a negative temperature sensitive polymer for use in the conjugate of the invention which is in turn used in the method of the invention is the desired temperature at which the conjugate exhibits phase transition as this will largely be dictated by the negative temperature sensitive polymer component of the conjugate.

In preferred embodiments of the invention, the conjugate precipitates at a temperature value between 35° C. and 65° C., preferably between 40° C. and 60° C., more preferably between 45° C. and 55° C., even more preferably between 48° C. and 52° C.

PCR is a technique used to make multiple copies of a specific DNA target from a longer sequence of DNA or a mixture of DNA molecules. Put another way, PCR is a method of amplifying a target nucleic acid in a DNA sample. The technique requires two short sequences of nucleotides, known in the art as primers or oligonucleotide primers, which provide a starting point for DNA synthesis. Primers are short sequences, usually around 20-25 nucleotides in length, of single-stranded DNA which are designed to flank the target DNA i.e. they are designed so that they are complementary to opposite strands of the target DNA at the end of the region to be copied. As such, one primer is referred to as the forward primer and the other the reverse primer. The PCR reaction is carried out by adding to a reaction vessel the template DNA containing the specific DNA target along with the two primers, deoxynucleotide triphosphates (dNTPs) e.g. dATP, dCTP, dGTP and dTTP, buffer (often containing $MgCl_2$) and DNA polymerase. Once prepared the reaction vessel is placed in a thermocycler which increases and decreases the temperature for predetermined periods of time. Firstly, the temperature is heated to around 90° C. or above in order to denature the template DNA i.e. separate the DNA duplex into single strands. This stage is commonly referred to as the 'denaturation phase'. The temperature is then lowered to around 55° C.-65° C. in order to allow the primers to anneal to the single stranded DNA. This stage is commonly referred to as the 'annealing phase'. The temperature is then increased to around 72° C. to allow the DNA polymerase to extend the primers and thus synthesize new strands of DNA. This stage is commonly referred to as the 'extension phase'. Once the extension phase is complete the cycle of denaturation, annealing and extension is repeated, usually between 25-35 times.

Reverse transcription PCR (RT-PCR) is a related technique which combines reverse transcription of RNA into complementary DNA (cDNA) with amplification of a target nucleic acid in a DNA sample. In RT-PCR, the RNA template is first converted to cDNA using reverse transcriptase. The cDNA is then used as a template in routine PCR, as described above.

In preferred embodiments of the invention, the DNA polymerase inhibitor is Zidovudine and the negative temperature sensitive polymer is PNiPMAM.

An advantage associated with the use of a conjugate comprising an inhibitor of DNA polymerase and a negative temperature sensitive polymer in PCR reactions is that the inhibitor remains viable when the temperature is increased. This is in direct contrast to the situation where e.g. an antibody is used to inhibit the DNA polymerase. When antibodies are used to inhibit the DNA polymerase, the increase in temperature causes an irreversible denaturing of the antibody. In contrast, the conjugate of the present invention which is used in the method of the invention remains viable throughout the PCR reaction, coming in and out of solution as and when required.

The DNA polymerase used in specific methods of the invention, the kit of the invention and the aqueous composition of the invention is preferably a thermostable/heat-stable DNA polymerase. Examples of species that such polymerases can be isolated from include *Thermus aquaticus, Pyrococcus furiosus, Thermococcus kodakaraensis Thermus thermophilus, Pyrococcus woesei, Thermus filiformis, Thermus flavus, Thermus ubiquitous, Thermus litoralis, Thermotoga maritima*. The DNA polymerase could also be a recombinant version of any of the aforementioned natural DNA polymerases. In preferred embodiments of the invention, the DNA polymerase is Taq polymerase.

A key step in the method of the invention is step (b) which involves heating the output of step (a) to a temperature at which the conjugate precipitates and thus the DNA polymerase is no longer inhibited. In preferred embodiments of the invention, the output of step (a) is heated to a temperature of at least 35° C., preferably at least 40° C., even more preferably at least 45° C. and most preferably at least 48° C. Accordingly, in preferred embodiments of the invention, the conjugate precipitates at a temperature of at least 35° C., preferably at least 40° C., even more preferably at least 45° C. and most preferably at least 48° C. Also preferably the conjugates precipitates at a temperature no higher than 60° C., suitably no higher than 55° C., or no higher than 52° C.

Step (c) of the PCR method involves performing standard PCR steps of denaturing the target nucleic acid, annealing the primers to the target nucleic acid, and extending the primers and then once the extension step is complete repeating the cycle of denaturation, annealing and extension at least two times. The number of times that step (c), thus the cycle of denaturation, annealing and extension, is repeated is dependent upon the amount of DNA template inputted into the reaction as well as the desired yield of PCR product. The lower the input, the higher the number of times that step (c) will need to be repeated. Similarly, the higher the desired yield of PCR product, the higher the number of times that step (c) will need to be repeated. In preferred embodiments of the invention step (c) is repeated at least ten times, even more preferably at least twenty times and most preferably at least thirty times.

The method used to prepare the conjugate of the present invention which is present in the kit and the aqueous composition of the present invention and used in the method of the invention is not critical as long as the DNA polymerase inhibitor and the negative temperature sensitive polymer are covalently conjugated. Methods of covalently conjugating molecules are well known to those of skill in the art. The conjugation can either be direct if the DNA polymerase inhibitor contains functional groups which permit conjugation to a negative temperature sensitive polymer or it can be indirect in that a linker can exist between the DNA polymerase inhibitor and the negative temperature sensitive polymer. In the conjugate of Example 1, the DNA polymerase inhibitor is conjugated to the polymer via a linker.

In preferred embodiments of the invention, the conjugate comprises the DNA polymerase inhibitor covalently attached at or near a terminus of the negative temperature sensitive polymer. Near in this context means within 20, preferably within 10, preferably within 5, more preferably within 2 monomers from a terminus of the negative temperature sensitive polymer.

Even more preferably, the conjugate comprises the DNA polymerase inhibitor covalently attached at a terminus of the negative temperature sensitive polymer. An advantage associated with this configuration is that the DNA polymerase inhibitor is more accessible to the DNA polymerase. To achieve this positioning of the DNA polymerase inhibitor vis-à-vis the negative temperature sensitive polymer, monomers are combined, and polymerisation carried out for a period of time prior to addition of the inhibitor, which is then incorporated into/conjugated to the polymer at or near its terminus.

EXAMPLES

The invention is now further described in specific examples with reference to the accompanying drawings in which:

FIG. 1 shows quantification of cDNA from a RTase reaction performed at different temperatures, with RTase alone or conjugated to zidovudine-poly-N-isopropylmethacrylamide; RTase cDNA was subsequently amplified and quantified by qPCR.

Example 1

Preparation of Thermo-Responsive zidovudine-poly-N-isopropylmethacrylamide Inhibitor

Step 1: Preparation of Polymerisable Zidovudine by Reaction with Propargyl Acrylate Propargyl acrylate (413 µL, 2 eq.) was added to ethanol (30 ml) in a sealable vessel and flushed with nitrogen for 5 minutes before zidovudine (0.50 g), copper sulfate (30 mg in water, 1 mol %) and sodium ascorbate (62 mg in water, 17 mol %) were added. The copper sulfate and sodium ascorbate can be added as a solid if enough water is added to the reaction to dissolve them both. The vessel was sealed and heated to 30° C. with gentle stirring and left overnight. The solvent was then partially evaporated using nitrogen gas (enough for a column, about 4 hours). Flash silica chromatography (100% ethyl acetate) was then used for purification and solvent was removed under reduced pressure at room temperature. A white solid of 0.332 g, (0.88 mmol, 47%) yield) was obtained.

Step 2: Free-Radical Polymerisation and Polymer Purification

In a glass vial, 26 mg polymerizable zidovudine, 50 mg of 1,1'-azobis(cyclohexanecarbonitrile) and 0.9 g N-isopropylmethacrylamide were dissolved using 20 ml of ethanol. The mixture was then bubbled with nitrogen for 5 min, sealed with a screw cap and placed in an oven at 70° C. for 24 hours. Polymer "P" was prepared as described above. Polymer "P1X" was prepared as above but the addition of 26 mg polymerizable zidovudine was done after 2 hours polymerisation. Polymer "P2X" was prepared as polymer "P1X" but adding 52 mg polymerizable zidovudine instead of 26 mg. After polymerisation all polymers were purified using the same protocol. For this, the polymerisation mixture was added to ca. 150 ml deionised water and the initial precipitate removed by filtration and discarded. The filter flow-through was then heated to 60° C. The precipitate formed was removed by filtration using a glass fibre membrane with a nominal pore size of 1.2 µm. After collection, the membrane was cooled to room temperature and the thermo-responsive polymer eluted with ethanol/water 50/50% (v/v). The obtained polymer had a lower critical solution temperature of approximately 52° C. as observed by formation of turbidity upon heating a polymer solution dispersed in water.

Example 2

Reverse Transcriptase (RTase) Reversible Inhibition Experiment Using Thermo-Responsive zidovudine-poly-N-isopropylmethacrylamide Inhibitor from Example 1

This example demonstrates the use of the thermo-responsive zidovudine-poly-N-isopropylmethacrylamide inhibitor from Example 1 for reversible inhibition of RTase.

The reaction was performed using the UltraScript 2.0 Reverse Transcriptase from PCR Bio (UK), according to the instructions of the manufacturer. General conditions were, for a 20 µl total reaction volume:

RNA=5 µg template plus random hexamer primers, in PCR Bio buffer mix.

PCR Bio RTase, 324 nM.

150 ng Zidovudine-poly-N-isopropylmethacrylamide.

RTase Reaction

The reaction was carried out at a range of temperatures below and above the LCST of the zidovudine-poly-N-isopropylmethacrylamide, to assess both inhibition and thermal reversibility of the conjugate. Individual reaction vials were kept at the set temperature for 30 min and the reaction allowed to proceed. The temperatures used were 25° C., 43° C., 55° C. and 35° C., the latter being done after the 55° C. step. After each incubation, 1-2 µl of cDNA product was taken for qPCR amplification and quantification. The results are presented in FIG. 1. Inhibition detected by observing loss of product peak.

Note that the zidovudine-poly-N-isopropylmethacrylamide prepared in Example 1 had a lower critical solution temperature of approximately 52° C., thus at temperatures above approximately 52° C., substantially all of the conjugate was out of solution.

This confirmed the dependence of temperature on RTase activity (availability) when RTase was conjugated to the thermally responsive polymer and that inhibition was reversible.

The invention claimed is:
1. A method of amplifying a target nucleic acid in a DNA sample comprising:
  (a) contacting the DNA sample containing the target nucleic acid with:
    (i) a DNA polymerase,
    (ii) at least two oligonucleotide primers designed to flank the target nucleic acid,
    (iii) a mixture of dATP, dGTP, dCTP, and dTTP, and
    (iv) a conjugate comprising a DNA polymerase inhibitor covalently attached to a negative temperature sensitive polymer,
  (b) heating the output of step (a) to a temperature at which the conjugate precipitates and thus the DNA polymerase is no longer inhibited, and
  (c) amplifying the target nucleic acid by performing PCR steps of denaturing the target nucleic acid, annealing the primers to the target nucleic acid, and extending the primers wherein step (c) is repeated at least two times.

2. The method of claim 1, wherein the DNA polymerase inhibitor is vidarabine, neobavaisoflavone, hexaprenylhydroquinone, aphidicolin or mithramycin A.

3. The method of claim 1, wherein the negative temperature sensitive polymer is selected from:
   (i) Poly(N-substituted acrylamide) s and its derivatives,
   (ii) Poly(methyl vinyl ether),
   (iii) Poly(N-vinylcaprolactam),
   (iv) Poly(2-substituted 2-oxazoline) s and its derivatives,
   (v) Poly(2-substituted 2-oxazine) s and its derivatives,
   (vi) Hydroxypropylmethyl cellulose,
   (vii) Ethylhydroxyethyl cellulose,
   (viii) Hydroxyethyl cellulose,
   (ix) Poly(asparagine) s and its derivatives, and
   (x) PNIPMAM.

4. The method of claim 1, wherein the conjugate precipitates at a temperature between 35° C. and 65° C.

5. The method of claim 1, wherein 1° C. above the precipitation temperature, 10% or less of the conjugate is in solution and 1° C. below the precipitation temperature, 90% or more of the conjugate is in solution.

6. The method of claim 1, wherein the conjugate comprises the DNA polymerase inhibitor covalently attached at or near a terminus of the negative temperature sensitive polymer.

7. The method of claim 1, wherein the DNA polymerase is Taq polymerase.

8. A kit comprising
   (a) a DNA polymerase, and
   (b) a conjugate comprising a DNA polymerase inhibitor covalently attached to a negative temperature sensitive polymer.

9. The kit of claim 8, wherein the conjugate precipitates at a temperature between 35° C. and 65° C.

10. The kit of claim 8, wherein the DNA polymerase inhibitor is vidarabine, lamivudine, zidovudine, neobavaisoflavone, hexaprenylhydroquinone, abacavir hemisulfate, aphidicolin, mithramycin A or tenofovir.

11. The kit of claim 9, wherein 1° C. above the precipitation temperature, 10% or less of the conjugate is in solution and 1° C. below the precipitation temperature, 90% or more of the conjugate is in solution.

12. The kit of claim 8, wherein the conjugate comprises the DNA polymerase inhibitor covalently attached at or near a terminus of the negative temperature sensitive polymer.

13. The kit of claim 8, wherein the DNA polymerase is Taq polymerase.

14. A method of reverse transcribing RNA comprising:
   (a) contacting an RNA sample with
      (i) a reverse transcriptase
      (ii) at least one primer
      (iii) a mixture of dATP, dGTP, dCTP and dTTP
      (iv) a conjugate comprising a reverse transcriptase inhibitor covalently attached to a negative temperature sensitive polymer,
   (b) heating the output of step (a) to a temperature at which the conjugate precipitates and thus the reverse transcriptase is no longer inhibited, and
   (c) incubating the output of step (b) for a sufficient time to allow reverse transcription to occur.

15. The method of claim 14, wherein the reverse transcriptase inhibitor is lamivudine, zidovudine, abacavir hemisulfate or tenofovir.

16. The method of claim 15, wherein the reverse transcriptase inhibitor is zidovudine.

17. The method of claim 14, wherein the negative temperature sensitive polymer is selected from:
   (i) Poly(N-substituted acrylamide) s and its derivatives,
   (ii) Poly(methyl vinyl ether),
   (iii) Poly(N-vinylcaprolactam),
   (iv) Poly(2-substituted 2-oxazoline) s and its derivatives,
   (v) Poly(2-substituted 2-oxazine) s and its derivatives,
   (vi) Hydroxypropylmethyl cellulose,
   (vii) Ethylhydroxyethyl cellulose,
   (viii) Hydroxyethyl cellulose,
   (ix) Poly(asparagine) s and its derivatives, and
   (x) PNiPMAM.

18. The method of claim 16, wherein the negative temperature sensitive polymer is PNiPMAM.

19. The method of claim 14, wherein the conjugate precipitates at a temperature of between 35° C. and 65° C.

20. The method of claim 14, wherein the time in step (c) is 30 minutes.

* * * * *